United States Patent [19]

Di Salvo

[11] 4,425,123

[45] Jan. 10, 1984

[54] PARENTERAL LIQUID APPLICATION APPARATUS

[75] Inventor: Francesco Di Salvo, Como, Italy

[73] Assignee: Sis-Ter S.p.A., Pignano, Italy

[21] Appl. No.: 325,777

[22] Filed: Nov. 30, 1981

[30] Foreign Application Priority Data

Dec. 30, 1980 [IT] Italy .............................. 26998 A/80

[51] Int. Cl.³ .............................................. A61M 5/14
[52] U.S. Cl. .................................... 604/247; 604/257;
604/251
[58] Field of Search ................ 604/246, 247, 251–254,
604/257; 137/510

[56] References Cited

U.S. PATENT DOCUMENTS

| | | | |
|---|---|---|---|
| 3,690,318 | 9/1972 | Gorsuch | 604/246 X |
| 3,931,818 | 1/1976 | Goldowsky | 604/254 |
| 4,186,740 | 2/1980 | Guerra | 604/246 X |
| 4,355,639 | 10/1982 | Di Salvo | 128/DIG. 13 |

Primary Examiner—Dalton L. Truluck
Attorney, Agent, or Firm—Frishauf, Holtz, Goodman & Woodward

[57] ABSTRACT

To provide for controlled application of parenteral fluid to a patient, in which the fluid is supplied from a flexible bag which changes its volume as the fluid is withdrawn therefrom, a liquid flow control device (2) has a membrane which, intermittently closes off and opens flow communication from beneath a dripping tube (1a) and a cannula (8) applying the liquid to the patient, the side of the membrane remote from its control side being connected by a capillary tube (15) to the interior of the dripping tube to equalize the pressure changes occurring on both sides of the membrane as the liquid level in the supply vessel decreases. The flow rate is initially adjusted by lowering the level of the liquid stabilization device with respect to the level of the dripping chamber.

11 Claims, 4 Drawing Figures

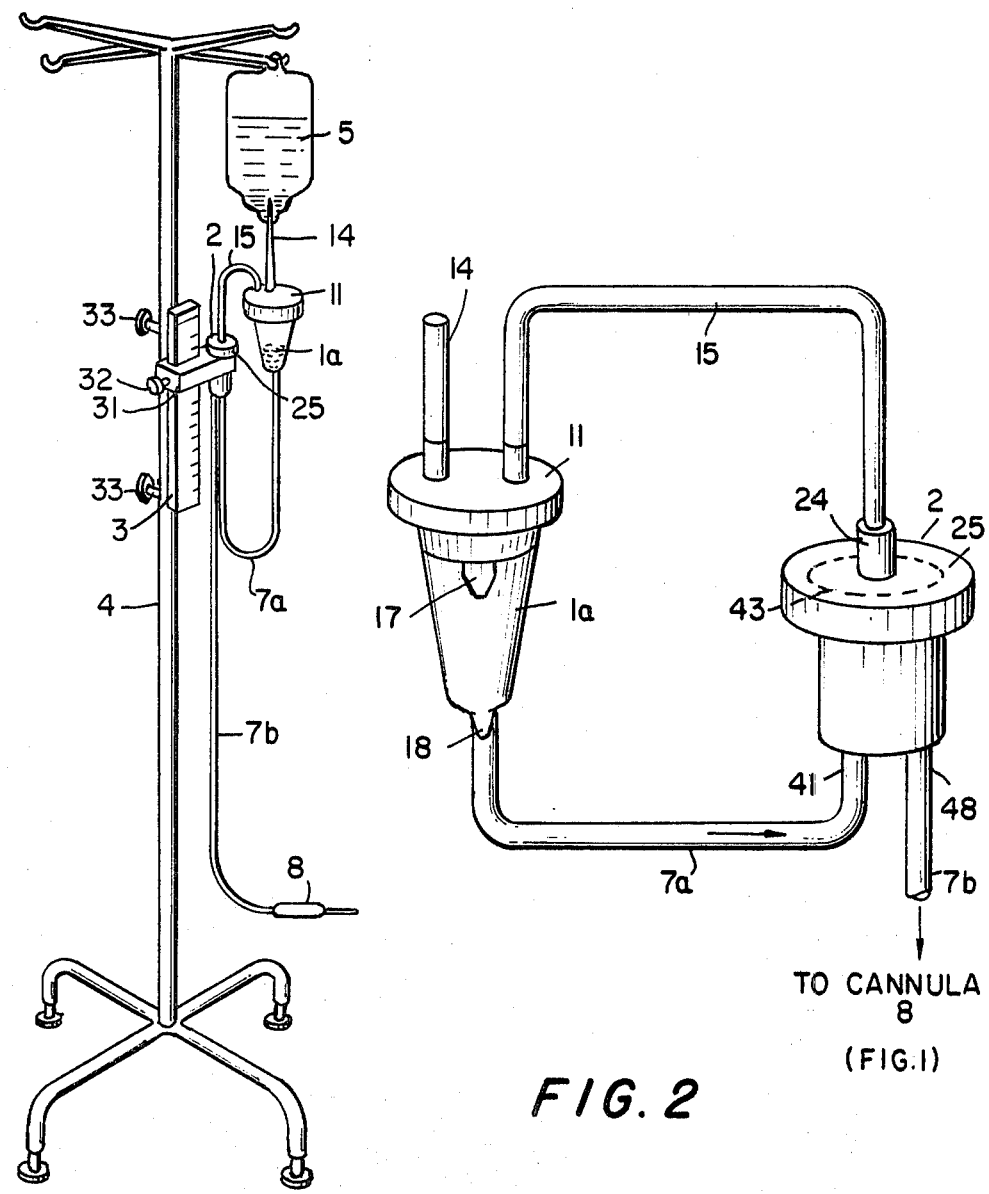

PARENTERAL LIQUID APPLICATION APPARATUS

The present invention relates to apparatus for the parenteral administration of liquids, and more particularly for the parenteral administration of liquids at an adjustable and accurately controllable flow rate from a limp or flexible container.

BACKGROUND

In my prior patent application U.S. Ser. No. 166842, filed July 8, 1980, now U.S. Pat. No. 4,355,639 "Apparatus for the Parenteral Administration of Liquids at a Constant, Adjustable Flow Rate", there is described an apparatus for accurately controlled administration of parenteral fluid, which is suitable for use with glass as well as with limp bottles, and which maintains the flow rate essentially constant throughout the period of time taken to empty the liquid container.

Some readjustment is desirable if the container is of the collapsing kind if the flow rate is to be maintained with extreme accuracy. The apparatus in accordance with the aforementioned application, now U.S. Pat. No. 4,355,639 uses a flow stabilization device which includes a body formed with a cavity therein to which a tubular inlet connects with the bottom of a dripping tube or funnel, an outlet passage is provided adapted for connection to a cannula for administration of liquid to a patient, and a flexible membrane, removably covering the opening of the outlet passage seals off the communication path between the inlet and the outlet, the other side of the membrane being exposed to ambient air.

THE INVENTION

It is an object to improve the apparatus of the aforementioned patent application by permitting use with both rigid as well as limp liquid supply vessels, without impairing the accuracy of administration of the fluid.

Briefly, the system as disclosed in the aforementioned application, now U.S. Pat. No. 4,355,639—the disclosure of which is hereby incorporated by reference—is modified by sealing the side of the membrane remote from the inlet and outlet passages with respect to ambient air, and providing a duct thereto so that pressure thereon can be equalized independently of air pressure, with pressure within the dripping chamber.

DRAWINGS

FIG. 1 is a perspective diagrammatic view of the complete apparatus of the present invention;

FIG. 2 is a front view, in greater detail, of components of the apparatus, including the feeding chamber or drip trough, and the flow stabilization device;

Figure 3:
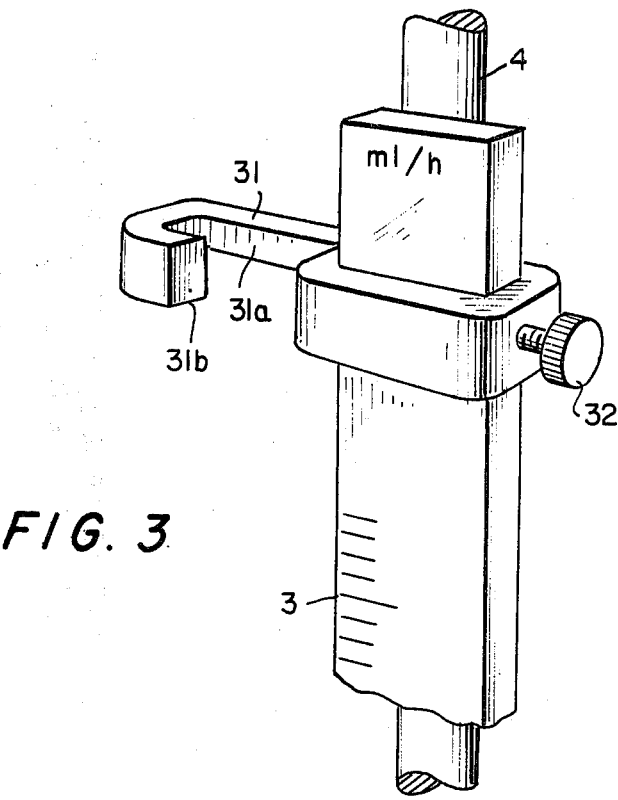
FIG. 3 is a detail view to an enlarged scale, showing the scale and the index rod with a sliding support for the stabilization device.

The basic apparatus is quite similar to that of the aforementioned application, now U.S. Pat. No. 4,355,639 and, as illustrated in FIG. 1, has a conventional, stationary support 4, to one arm of which a vessel of the liquid to be administered is secured. This vessel may be a rigid structure, such as a glass bottle, or may be a flexible bag, for example a flexible plastic bag 5. The vessel 5 is connected by a tube 14 to a dripping chamber 1a. The dripping chamber has a top sealed covering, for example a ring nut 11, through which two tubes pass, one being tube 14. The other tube 15 is connected to a flow stabilization device 2, secured to a bracket 31 which is adjustably positioned on a scale carrier 3. The bracket 31 can be locked in position by a locking screw 32, engaging the scale carrier 3. The scale carrier 3, in turn, is secured to the support 4, for example by one or more screws 33, permitting, however, sliding of the carrier 31 on scale 3.

The liquid from vessel 5 enters the vessel or cup 1a through a perforated end member 17 (FIG. 2) having, preferably but not necessarily, a diameter of from between 0.3 to 3 mm. The cup or dripping chamber 1a can be made of a flexible or rigid plastic material. At its bottom it has an end element 18 arranged for coupling to a tube 7a to introduce the liquid into the flow rate adjusting and stabilization device 2.

Figure 4:
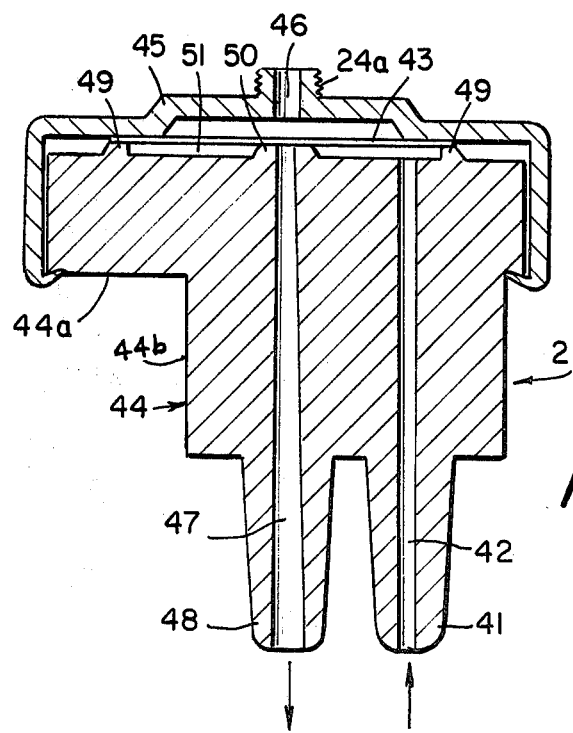
FIG. 4 is a sectional view of a preferred embodiment of the flow stabilization device.

The adjusting and stabilization device 2—see specifically FIG. 4—comprises a holder body 44 with two tubular passages 42, 47 therethrough, and a cap element 45 thereover. The upper face of the body 44 has an annular ring-like projection 49 and a central projection 50. A membrane 43 is positioned over the ring 49 and over the projection 50. The membrane 43 is made of any suitable flexible material which is chemically inert with respect to the liquid to be administered.

The cap 45 is firmly secured to the body 44, thereby locking the membrane 43 along the circular zone or rim between the annular projection 49 and the corresponding opposite zone of the cap 45.

The membrane 43 merely rests on the central projection 50. Cap 45 has a central opening 46 which has a projecting connecting portion 24a, for example threaded or ridged.

In accordance with the present invention, the opening 46 is placed in pneumatic communication with the drip tube or vessel 1a by connecting a fitting 24 to the connecting portions 24a, and tube 15 from fitting 24 to the drip vessel 1a.

The lower face of the membrane 43 and the upper face of the body 44 between the annular projection 49 and the central projection 50 defines an annular chamber 51 into which the upper end of passage 42 extends. Passage 42 is, preferably, of smaller diameter than passage 47 through the body 44, and may be of capillary size. The upper end of tubular passage 47 leads into the central zone of the projection 50, in contact with the membrane. The opposite end of the narrower passage 42 and of the tubular passage 47 lead, respectively, to connectors 41 and 48, as schematically shown by the arrows in FIG. 4. Connector 41 is connected to the inlet duct 7a, connector 48 to the outlet duct 7b which, in turn, is in communication with a cannula or needle 8 for the parenteral administration of the liquid from bag 5, FIG. 1.

In accordance with a feature of the invention, the duct or tube 15 has only a very small inner diameter, almost of capillary size, such that pressure variations in the inside of the dripping chamber are transmitted essentially instantaneously to the upper side of the membrane 43 of the flow adjusting device 2 of FIG. 4.

Operation: The scale 3 is secured to the rod 4 at a suitable height, for example by suitable placement of screws 33—which may have a shoulder to permit ready sliding of the carrier 31 with respect to the scale 3. The position of the scale 3 can be changed to accommodate different heights of positioning of a patient. The position of the flow control device 2, locked in bracket 31, is then calibrated by moving the bracket 31 along the scale rod 3. This calibration is carried out by locating the level in the liquid in the dripping chamber 1a and the flow rate adjusting and stabilization device 2 at the same level. In this position, no flow of liquid through the stabilization device 2 will occur, since the pressures exerted on the two face of the membrane 43 are equal. Accordingly, the membrane prevents liquid flowing from duct 42 into duct 47. This pressure value depends on the level of the liquid in the vessel 5. Since, as is assumed, no liquid is being supplied, this pressure is a constant.

When it is desired to administer the parenteral liquid, the slider 31 is displaced, after loosening nut 32, to a lower position on the graduated scale rod 3, to a position in accordance with the desired flow rate. The sliding member 31, with the flow adjusting device 2 thereon, is then locked in position. Due to the level difference between the liquid level in the dripping chamber 1a and of the membrane 43, a pressure difference will build up on the two sides of the membrane which will allow liquid to flow through the passages 41, ring space 51, and out through passage 47, since the membrane will lift off slightly from its seat at the projection 50 about the duct 47. The pressure on the top side of the membrane—with respect to FIG. 4—is applied thereto through duct 15. It is that pressure which is present in the upper portion of the dripping chamber 1a, and will depend on the liquid level in the vessel 5. At the start of the delivery, this pressure, of course, is equal to be calibration pressure.

The pressure acting on the lower side of the membrane corresponds to the sum of the fixed pressure due to the raised level in the vessel 5 and to the pressure derived from the difference in height between the liquid in the dripping chamber 1a and the position of the membrane. The difference between these values, which will depend on the position, that is, on the height of the flow rate adjusting device 2, is the over-pressure value which causes the membrane to deform and permits liquid to flow.

During liquid dispensation, and as the liquid level in the vessel 5 decreases, the pressure in the dripping chamber 1a, and hence the pressure exerted on the top of the membrane through the duct also will decrease. The flow rate, however, does not change, since the pressure decrease is compensated by a corresponding or similar pressure decrease on the lower face of the membrane, as transmitted thereto by fluid flowing through duct 7a and through the inlet duct 42. Each pressure variation in the dripping chamber 1a, and in particular at the liquid inlet zone therof, is transmitted simultaneously to the two faces of the membrane—through the liquid in the duct 7a and through the tube 15—so that the membrane will deflect and open the liquid passage only as a function of the pressure difference determined by the relative level or height of the liquid within the dripping tube 1a and of the membrane 43 of the flow adjusting device 2. Thus, adjustment of the position of the device 2, by setting of the set screw 32 and clamping the holder bracket 31 in position, will provide for an invarying flow rate of liquid through the outflow duct 47 to the cannula 8.

In accordance with the present invention, thus, a feedback circuit is provided effective to transmit the same pressure values which change in time as the liquid is administered to the two faces of the membrane. Thus, and because of this feedback, no change in the pressure differential as determined by position of the device 2 along the graduated scale rod 3 will be needed to maintain a constant flow rate.

At the end of the liquid dispensing operation, and since the system is a closed one, no air will enter the dripping chamber, and none will enter the patient's veins. The flexible bag 5 will merely collapse.

The system may be used, of course, also with a rigid-wall vessel, such as a glass bottle. Since, in a rigid-wall vessel, a passage is provided for the inlet of air, the pressure will not decrease as the level of the liquid in the vessel decreases but, on the contrary, it will remain constant and, specifically, equal to atmospheric pressure. This value, as aforesaid, will be transmitted in the same manner on the two faces of the membrane and the parameter determining the flow rate will, also in that case, be the level difference between the flow rate adjusting device 2 and the liquid level in the dripping chamber 1a. Calibration will be identical to that described in connection with the flexible bag.

A precisely constant flow rate can be maintained for long periods of time by the simple calibrating procedure, which does not involve test administration of the liquid within vessel 5. Flow rates which may be excessive and dangerous to a patient can be readily avoided. The flow rate can be easily adjusted by merely shifting the bracket 31, and with it the device 2 longitudinally along the scale rod 3.

The tube 15 passing through cap 11, which may be of metal or plastic, is a flexible tube joining the connector 24 to the connection stub 24a. This tube provides for communication from the inside of the drip tube or reservoir 1a to the upper side of the membrane 43 to provide for pressure equalization between the drip tube 1a and the upper side of the membrane. The tube 15 can terminate below cap 11 and in the space between the perforated end member 17 and the top of the drip tube 1a.

The upper portion 44a of body 44 preferably is circular; the lower portion 44b, however, can be flattened and made to fit into the bent-over portion 31b of bracket 31 (FIG. 3) to be slipped in between the bent-over portion and the back wall 31a of the bracket, and to be seated securely therein.

I claim:
1. Apparatus for the parenteral administration of a liquid at a constant, adjustable flow rate comprising
   means (5, 14) supplying said liquid by gravity flow;
   a dripping tube or funnel (1a) defining a dripping chamber in liquid communication with and positioned below said liquid supply means;
   support means (4) supporting said liquid supply means and said dripping tube or funnel, and positioning said dripping tube or funnel (1a) at a predetermined level or elevation;
   fluid connection means (7a) connected to an outlet of the dripping tube or funnel (1a);
   a flow stabilization device including
   a body (44) formed with a cavity therein, a tubular inlet passage (41) connected to the fluid connection means (7a) and thus connecting said cavity with the bottom of said dripping tube or funnel (1a), a tubular outlet passage (47) connecting said cavity to a tubing (7b), adapted for connection to a cannula (8) for administration of the liquid to a patient, said inlet passage (42) having a smaller diameter than the outlet passage (47), and a flexible membrane (43) removably covering the opening of the outlet passage (47) within the cavity and closing off said cavity;

a stationary scale (3) vertically positioned at a controlled level with respect to said predetermined level or elevation;

a slider (31) slidable vertically with respect to said stationary scale, said stabilization device being vertically adjustably supported on said slider;

means (32) for securing said slider (31) and hence said stabilization device (2) in vertically adjustable position with respect to said scale, and hence with respect to said predetermined level or elevation of the dripping tube or funnel (1a) to permit reproducibly adjustably positioning of said stabilization device at a level below said predetermined level to permit controlled flow from said dripping tube or funnel (1a) to and through said stabilization device (2) as a function of level difference between the liquid level in said dripping tube or funnel (1a) and said stabilization device (2);

and comprising, in accordance with the invention, pneumatic connection means (24, 24a, 15) connecting the side of the membrane (43) remote from the outlet passage with the dripping tube or funnel to equalize pressure within the dripping tube or funnel and the side of the membrane remote from said tubular outlet passage and thereby compensate for variation in the pressure of liquid supplied through the inlet passage (42) of said device as the liquid level in said supply means changes.

2. Apparatus according to claim 1, wherein said pneumatic communication means comprises a tubular duct (15) having one end connected through the cover of said dripping tube or funnel (1a);

and the other end to said flow stabilization device and in pneumatic communication with the side of the membrane (43) remote from the outlet passage in said device.

3. Apparatus according to claim 2, wherein said duct is of the capillary type and dimensional to transmit pressure values present in the inside of the dripping chamber (1a) practically instantaneously to the membrane (43).

4. Apparatus according to claim 1, wherein the dripping chamber includes a drip member (17) having an opening therein of a diameter of from about 0.3 to 3 mm.

5. Apparatus according to claim 1, wherein said slider (31) has a hook member (31b) shaped to form a seat;

and said flow stabilization device (2) has a shaped portion (44b) fitting said seat.

6. Apparatus according to claim 1, wherein said stationary scale is vertically positioned on said support means (4).

7. Apparatus according to claim 1, wherein the dripping tube or funnel (1a) includes a drip member (17);

and the communication means (15) communicates with the interior of the dripping chamber in the zone between the opening of the drip member and the top of the dripping tube or funnel to transmit pneumatic pressure within said dripping tube or funnel to the membrane.

8. Apparatus according to claim 7, wherein said pneumatic communication means comprises a tubular duct (15) having one end connected through the cover of said dripping tube or funnel (1a);

and the other end to said flow stabilization device and in pneumatic communication with the side of the membrane (43) remote from the outlet passage in said device.

9. Apparatus according to claim 8, wherein said duct is of the capillary type and dimensioned to transmit pressure values present in the inside of the dripping chamber (1a) practically instantaneously to the membrane (43).

10. Apparatus according to claim 9, wherein the drip member (17) has an opening therein of a diameter of from 0.3 to 3 mm.

11. Apparatus according to claim 7, wherein the drip member (17) has an opening therein of a diameter of from 0.3 to 3 mm.

* * * * *